US006136540A

United States Patent [19]
Tsipouras et al.

[11] Patent Number: 6,136,540
[45] Date of Patent: Oct. 24, 2000

[54] AUTOMATED FLUORESCENCE IN SITU HYBRIDIZATION DETECTION OF GENETIC ABNORMALITIES

[75] Inventors: Petros Tsipouras, Farmington, Conn.; Triantafillos P. Tafas, Athens, Greece

[73] Assignee: Ikonisys Inc., New Haven, Conn.

[21] Appl. No.: 09/251,358

[22] Filed: Feb. 17, 1999

Related U.S. Application Data

[63] Continuation of application No. 08/689,562, Aug. 12, 1996, abandoned, which is a continuation of application No. 08/316,778, Oct. 3, 1994, abandoned.

[51] Int. Cl.⁷ .................................................. C12Q 1/68
[52] U.S. Cl. ............................ 435/6; 435/69.1; 435/91.1; 435/91.2; 395/13; 359/629; 364/400; 536/23.1; 536/24.3; 536/24.31; 536/24.32; 536/24.33
[58] Field of Search ........................... 435/6, 69.1, 91.1, 435/91.2; 395/13; 359/629; 364/400; 128/922; 536/23.1, 24.3, 24.31, 24.32, 24.33; 935/77, 78; 436/501; 313/504, 505; 382/49

[56] References Cited

U.S. PATENT DOCUMENTS

| | | | |
|---|---|---|---|
| 3,879,706 | 4/1975 | Favier et al. | 240/146.3 |
| 4,122,518 | 10/1978 | Castleman et al. | 364/300 |
| 4,175,860 | 11/1979 | Bacus | 356/39 |
| 4,400,370 | 8/1983 | Kass | 424/3 |
| 4,523,278 | 6/1985 | Reinhardt et al. | 364/413 |
| 4,615,878 | 10/1986 | Kass | 424/3 |
| 4,656,594 | 4/1987 | Ledley | 364/498 |
| 4,675,286 | 6/1987 | Calenoff | 435/7 |
| 4,741,043 | 4/1988 | Bacus | 382/6 |
| 4,866,785 | 9/1989 | Shibano | 382/49 |
| 4,874,693 | 10/1989 | Bogart | 435/7 |
| 4,965,725 | 10/1990 | Rutenberg | 364/413.1 |
| 4,983,044 | 1/1991 | Schweber | 356/443 |
| 4,996,040 | 2/1991 | Kass | 424/3 |
| 5,000,192 | 3/1991 | Sealfon | 128/760 |
| 5,004,681 | 4/1991 | Boyse et al. | 435/2 |
| 5,008,185 | 4/1991 | Bacus | 435/7.23 |
| 5,018,209 | 5/1991 | Bacus | 382/6 |
| 5,041,733 | 8/1991 | Naguchi et al. | 250/461.2 |
| 5,073,857 | 12/1991 | Peters et al. | 364/413.1 |
| 5,077,806 | 12/1991 | Peters et al. | 383/8 |
| 5,109,429 | 4/1992 | Bacus et al. | 382/6 |
| 5,153,117 | 10/1992 | Simons | 435/2 |
| 5,192,553 | 3/1993 | Boyse et al. | 424/529 |
| 5,204,884 | 4/1993 | Leary et al. | 377/10 |
| 5,225,326 | 7/1993 | Bresser et al. | 435/6 |
| 5,252,487 | 10/1993 | Bacus et al. | 436/63 |
| 5,287,272 | 2/1994 | Rutenberg et al. | 364/413.01 |
| 5,294,870 | 3/1994 | Tang et al. | 313/504 |
| 5,472,842 | 12/1995 | Stokke et al. | 435/6 |
| 5,756,696 | 5/1998 | Gray et al. | 536/23.1 |

FOREIGN PATENT DOCUMENTS

| | | |
|---|---|---|
| 0421736 | 4/1991 | European Pat. Off. . |
| 0 512 965 A1 | 11/1992 | European Pat. Off. . |
| WO 92/13308 | 8/1992 | WIPO . |
| WO 93/06245 | 4/1993 | WIPO . |
| WO 93/21345 | 10/1993 | WIPO . |
| WO 94/02646 | 2/1994 | WIPO . |
| WO 94/02829 | 2/1994 | WIPO . |
| WO 94/02830 | 2/1994 | WIPO . |

OTHER PUBLICATIONS

Lockett et al., Analytical and Quantitative Cytology and Histology, vol. 13, No. 1, pp. 29–44, Feb. 1991.
Lockett et al., Quantitative Precision of an Automated Fluorescence–Based Image Cytometer, vol. 14, No. 3, pp. 187–202, Jun. 1992.
Lockett et al., Automated Image–Based Cytometry with Fluoroscence–Stained Specimens, BioTechniques, vol. 10, No. 4, pp. 514–519, 1991.
Poon, et al., Automated Image Detection and Segmentation in Blood Smears, Cytometry, vol. 13, pp. 766–774, 1992.
Neuromedical Systems, Inc., The breakthrough in automated Pap smear screening, 1989/1990, 5 pages.
Parthenis et al., Blood analysis using black and white digital images, J. Biomed. Eng., vol. 14, pp. 287–292, Jul., 1992.
Abstract: Sigma Diagnostics, Alkaline Phosphatase, Leukocyte, Procedure No. 86, Oct., 1990, 4 pages.
Media Cybernetics, Image–Pro Plus Manual, pp. 6–12–6–13, 6–39–8–43, A–21–A–23.
Clinical Chemistry, Measuring Unconjugated Estriol in Maternal Serum to Screen For Fetal Down Syndrome, vol. 38, No. 9, 1992, pp. 1687–1689.
The Lancet, Urea–Resistant Neutrophil Alkaline Phosphatase in Mothers with Trisomy 21 Pregnancy, Oct. 1, 1983, pp. 799–800.
The Lancet, Semi–quantitative detection of Down's syndrome with PCR, vol. 340, Sep. 5, 1992, pp. 620–621.
Prenatal Diagnosis, First–Trimester Maternal Serum Biochemical Indicators in Down Syndrome, Prenatal Diagnosis, vol. 10, 1990, pp. 245–251.
Prenatal Diagnosis, vol. 11, Cu/Zn Superoxide Dismutase Quantification from Fetal Erythrocytes—An Efficient Confirmatory Test for Down's Syndrome After Maternal Serum Screening and Sonographic Investigations, 1991, pp. 295–303.
"Measuring Unconjugated Estriolin Maternal Serum to Screen for Fetal Down Syndrome", Clin Chem 38/9, 1687–1689 (1992), Cuckle.

(List continued on next page.)

Primary Examiner—Kenneth R. Horlick
Assistant Examiner—Janell E. Taylor
Attorney, Agent, or Firm—Pennie & Edmonds LLP

[57] ABSTRACT

Automated sample analysis is performed by a computer-implemented apparatus and method for distinguishing objects of interest in an optical field from other objects and background in the optical field, collectively called background. Once an object has been identified, the color comprised of a combination of the red, green and blue components of the pixels occupied by the image of the object of interest, or another parameter of interest relative to that object can be measured and stored. This computer-implemented analysis apparatus and method is performed on objects of interest in the sample which are tagged using fluorescent tags. The sample may be a cell sample containing a nucleic acid target and the tagging achieved by fluorescence in situ hybridization.

20 Claims, 6 Drawing Sheets

OTHER PUBLICATIONS

Lichter P, Boyle A1, Cremer T, Ward DC (1991) Analysis of Genes and Chromosomes by Nonisotopic in situ Hybridization, Genet Anal Techn Appl 8(1): 24–35.

du Manoir S., Speicher MR, Joos S, et al (1993) Detection of complete and partial chromosome gains and losses by comparative genomic in situ hybridization, Hum Genet 90; 590–610.

Wilson et al. (ed.); Harrison's Principles of Internal Medicine. New York, McGraw–Hill, 1991.

AUTOMATED FLUORESCENCE IN SITU HYBRIDIZATION DETECTION OF GENETIC ABNORMALITIES

This application is a continuation of U.S. patent application Ser. No. 08/689,562 filed Aug. 12, 1996, currently abandoned, which is a continuation of U.S. patent application Ser. No. 08/316,778 filed Oct. 3, 1994, currently abandoned.

FIELD OF THE INVENTION

The present invention relates to a computer-implemented method and apparatus for distinguishing objects of interest from other objects and background in an optical field. More particularly, the invention relates to a computer-implemented method of identifying, characterizing and counting objects in the optical field which are tagged using fluorescence in situ hybridization to specifically visualize selected objects in the optical field. In particular, the invention relates to the use of such a computer-implemented method and apparatus for determining genetic abnormalities.

BACKGROUND OF THE INVENTION

The normal human complement of chromosomes consists of the sex chromosomes (designated X and Y) and 22 autosomes (numbered 1–22). It has been estimated that a minimum of 1 in 10 human conceptions has a chromosome abnormality. As a general rule, an abnormal number of sex chromosomes is not lethal, although infertility can result. In contrast, an abnormal number of autosomes typically results in early death. Of the three autosomal trisomies found in live-born babies (trisomy 21, 18 and 13), only individuals with trisomy 21 (more commonly known as Down syndrome), survive past infancy.

Although Down syndrome is easily diagnosed after birth, prenatal diagnosis is problematic. To date, karyotyping of fetal cells remains the established method for the diagnosis of Down syndrome and other genetic abnormalities associated with an aberration in chromosomal number and/or arrangement. Such genetic abnormalities include, for example, chromosomal additions, deletions, amplifications, translocations and rearrangements. The assessment of such abnormalities is made with respect to the chromosomes of a healthy individual, i.e., an individual having the above-described normal complement of human chromosomes.

Genetic abnormalities include the above-noted trisomies, such as Down syndrome, as well as monosomies and disomies. Genetic abnormalities also include additions and/or deletions of whole chromosomes and/or chromosome segments. Alterations such as these have been reported to be present in many malignant tumors. Thus, aberrations in chromosome number and/or distribution (e.g., rearrangements, translocations) represent a major cause of mental retardation and malformation syndromes (du Manoir et al., et al., Human Genetics 90(6): 590–610 (1993)) and possibly, oncogenesis. See also,. e.g., (Harrison's Principles of Internal Medicine, 12th edition, ed. Wilson et al., McGraw Hill, N.Y., N.Y., pp. 24–46 (1991 )), for a partial list of human genetic diseases that have been mapped to specific chromosomes, and in particular, for a list of X chromosome linked disorders. In view of the growing number of genetic disorders associated with chromosomal aberrations, various attempts have been reported in connection with developing simple, accurate, automated assays for genetic abnormality assessment.

In general, karyotyping is used to diagnose genetic abnormalities that are based upon additions, deletions, amplifications, translocations and rearrangements of an individual's nucleic acid. The "karyotype" refers to the number and structure of the chromosomes of an individual. Typically, the individual's karyotype is obtained by, for example, culturing the individual's peripheral blood lymphocytes until active cell proliferation occurs, preparing single, proliferating (e.g. metaphase, and possibly, interphase) cells for chromosome visualization, fixing the cells to a solid support and subjecting the fixed cells to in situ hybridization to specifically visualize discrete portions of the individual's chromosomes.

The rapid development of non-isotopic in situ hybridization techniques and the general availability of an ever-expanding repertoire of chromosome-specific DNA probes have extended the number of genetic disorders for which karyotyping is feasible. See, e.g., Lichter et al., "Analysis of Genes and Chromosomes by Non-isotopic in situ Hybridization", GATA 8(1): 24–35 (1991). Such methods include the use of probe sets directed to chromosome painting for visualizing one or more preselected chromosomal subregions in a targeted fashion. Methods such as these require at least a modicum of knowledge regarding the types of aberration(s) expected in order to select useful DNA probes complementary to target nucleic acids present in a clinical or tumor cell sample.

Nucleic acid hybridization techniques are based upon the ability of a single stranded oligonucleotide probe to base-pair, i.e., hybridize, with a complementary nucleic acid strand. Exemplary in situ hybridization procedures are disclosed in U.S. Pat. No. 5,225,326 and copending U.S. patent application Ser. No. 07/668,751, the entire contents of which are incorporated herein by reference. Fluorescence in situ hybridization ("FISH") techniques, in which the nucleic acid probes are labeled with a fluorophor (i.e., a fluorescent tag or label that fluoresces when excited with light of a particular wavelength), represents a powerful tool for the analysis of numerical, as well as structural aberrations chromosomal aberrations. See, e.g., PCT Application WO 94/02646, inventors M. Asgari et al., published Feb. 3, 1994, (hereinafter, "Asgari") co-pending U.S. patent application Ser. No. 07/915,965; P. Lichter, et al., Genet. Anal. Tech. Appl. 8: 24–35 (1991); and S. Du Manoir, et al., Human Genetics 90(6): 590–610 (1993), the entire contents of which publications are incorporated herein by reference.

Asgari reports in situ hybridization assays for determining the sex of a fetus, genetic characteristics or abnormalities, infectious agents and the like, by nucleic acid hybridization of fetal cells such as those circulating in material blood. The fetal cells are distinguished from maternal cells present in the fixed sample by staining with an antibody which specifically recognizes the maternal or fetal cell or by in situ hybridization to detect one or more fetal mRNAs. The method reportedly is useful for detecting chromosomal abnormalities in fetal cells. However, the fetal cells must be enriched prior to analysis.

PCT Application WO 94/02830, inventors M. Greaves, et al., published Feb. 3, 1994, (hereinafter, "Greaves") report a method for phenotyping and genotyping a cell sample. The method involves contacting a fixed cell with an antibody labeled with a first fluorophor for phenotyping the cell via histochemical staining, followed by contacting the fixed cell with a DNA probe labeled with a second fluorophor for genotyping the cell. The first and second fluorophors fluoresce at different wavelengths from one another, thereby allowing the phenotypic and genetic analysis on the identical fixed sample.

Despite the above-described advances in the development of fluorescent in situ hybridization methods for the diagnosis of genetic abnormalities, the analysis of the fluorophor-labeled sample remains labor-intensive and involves a significant level of subjectivity. This is particularly true in connection with the prenatal diagnosis of genetic abnormalities in which fetal cells must either be isolated from maternal cells or visually distinguished therefrom prior to assessment for genetic abnormalities. Thus, for example, a laboratory technician must manually prepare and sequentially stain the sample (first, with a histochemical stain to phenotype the cells, second, with a hybridization probe to genotype the cell); visually select fetal cells from other cells in the optical field (using, for example, the above-mentioned histochemical staining procedure); assess the relative distribution of fluorescent color that is attributable to hybridization of the fluorophor-tagged probe; and compare the visually-perceived distribution to that observed in control samples containing a normal human chromosome complement. As will be readily apparent, the above-described procedure is quite time-consuming. Moreover, because the results are visually-perceived, the frequency of erroneous results can vary from one experiment to the next, as well as from one observer to the next.

SUMMARY OF THE INVENTION

The instant invention overcomes these and other problems by providing computer-implemented methods for determining genetic abnormality which thereby eliminate subjective analysis of selectively stained chromosomes. More specifically, a method for detecting whether a genetic abnormality is present in a fixed sample containing at least one target nucleic acid is provided. The method involves (i) receiving a digitized color image of the fixed sample, which has been subjected to fluorescence in situ hybridization under conditions to specifically hybridize a fluorophor-labeled probe to the target nucleic acid; (ii) processing the color image in a computer to separate objects of interest from background in the color image; (iii) measuring parameters of the objects of interest so as to enumerate objects having specific characteristics; and (iv) analyzing the enumeration of objects with respect to a statistically expected enumeration to determine the genetic abnormality. The numerical distribution of target nucleic acid is indicative of the genetic abnormality. The method is useful for diagnosing genetic abnormalities associated with an aberration in chromosomal number and/or arrangement. Such "genetic abnormalities" include, for example, chromosomal additions, deletions, amplifications, translocations and rearrangements with respect to the chromosomes of a healthy individual, i.e., an individual having the above-described normal complement of human chromosomes.

BRIEF DESCRIPTION OF THE DRAWINGS

Embodiments of the present invention will now be discussed in connection with the figures. Like reference numerals indicate like elements in the figures, in which.

DETAILED DESCRIPTION

Figure 1:
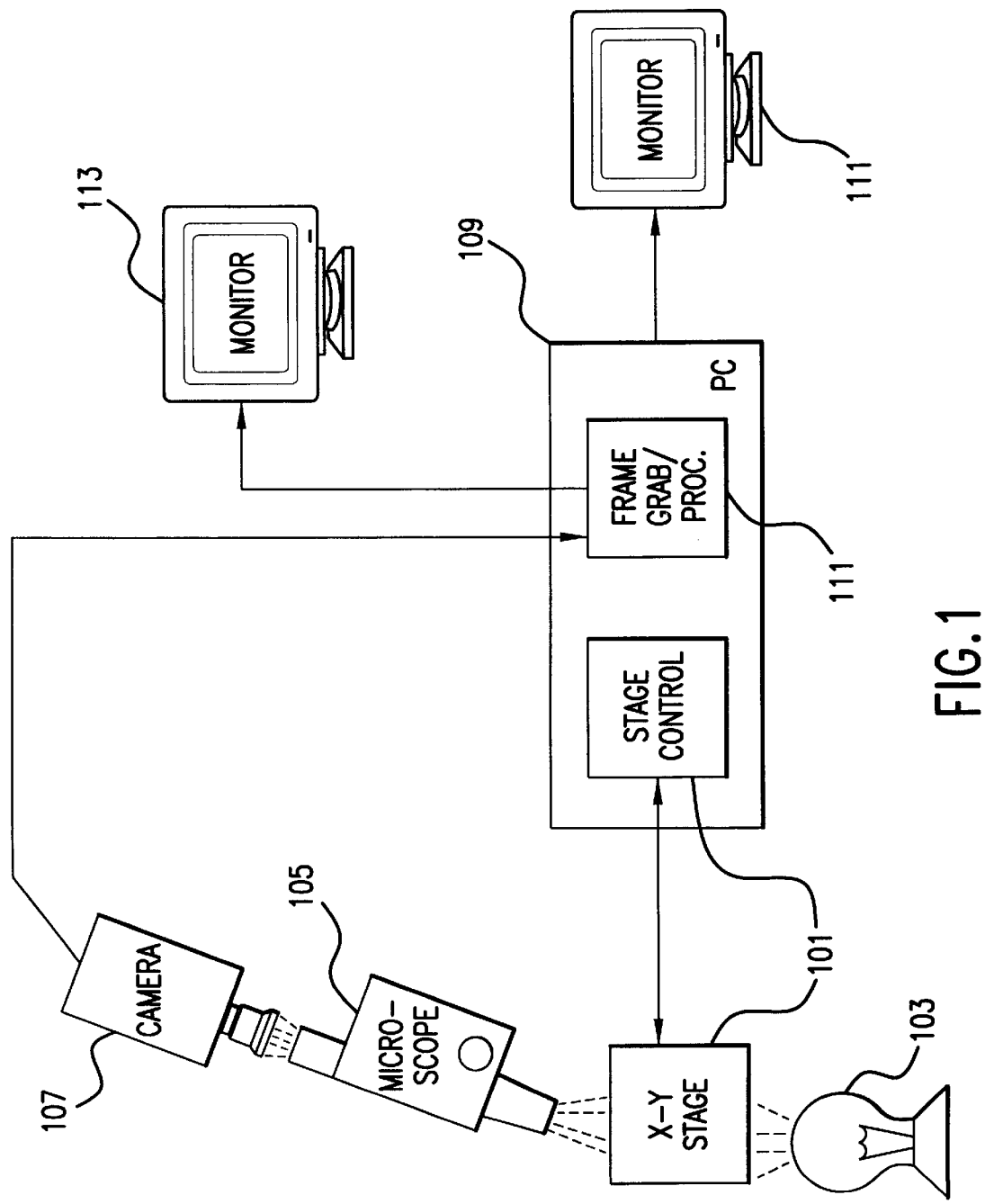
FIG. 1 is a block diagram of one embodiment of the apparatus of the invention.

A method for detecting whether a genetic abnormality is present in a fixed sample is disclosed herein. The method involves (i) receiving a digitized color image of the fixed sample, which has been subjected to fluorescence in situ hybridization under conditions to specifically hybridize a fluorophor-labeled probe to the target nucleic acid; (ii) processing the color image in a computer to separate objects of interest from background in the color image; (iii) measuring parameters of the objects of interest so as to enumerate objects having specific characteristics; and (iv) analyzing the enumeration of objects with respect to a statistically expected enumeration to determine the genetic abnormality. The method is useful for diagnosing genetic abnormalities associated with an aberration in chromosomal number and/or arrangement. Thus, for example, the invention can be used to detect chromosomal rearrangements by using a combination of labeled probes which detect the rearranged chromosome segment and the chromosome into which the segment is translocated.

As used herein, "genetic abnormalities" refers to an aberration in the number and/or arrangement of one or more chromosomes with respect to the corresponding number and/or arrangement of chromosomes obtained from a healthy subject, i.e., an individual having a normal chromosome complement. Genetic abnormalities include, for example, chromosomal additions, deletions, amplifications, translocations and rearrangements that are characterized by nucleotide sequences of as few as about 15 base pairs and as large as an entire chromosome.

The method is useful for determining one or more genetic abnormalities in a fixed sample, i.e., a sample attached to a solid support which has been treated in a manner to preserve the structural integrity of the cellular and subcellular components contained therein. Methods for fixing a cell containing sample to a solid support, e.g., a glass slide, are well known to those of ordinary skill in the art.

The sample contains at least one target nucleic acid, the distribution of which is indicative of the genetic abnormality. By "distribution", it is meant the presence, absence, relative amount and/or relative location in one or more nucleic acids (e.g., chromosomes) known to include the target nucleic acid. In a particularly preferred embodiment, the target nucleic acid is indicative of a trisomy 21 and thus, the method is useful for diagnosing Down syndrome. In a particularly preferred embodiment, the sample intended for Down syndrome analysis is derived from maternal peripheral blood. More particularly, lymphocytes are isolated from peripheral blood according to standard procedures, the cells are attached to a solid support (e.g., by centrifuging onto glass slides), and fixed thereto according to standard procedures (see, e.g., the Examples) to permit detection of the target nucleic acid.

Fluorescence in situ hybridization refers to a nucleic acid hybridization technique which employs a fluorophor-labeled probe to specifically hybridize to and thereby, facilitate visualization of, a target nucleic acid. Such methods are well known to those of ordinary skill in the art and are disclosed, for example, in U.S. Pat. No. 5,225,326; U.S. patent application Ser. No. 07/668,751; PCT WO 94/02646, the entire contents of which are incorporated herein by reference. In general, in situ hybridization is useful for determining the distribution of a nucleic acid in a nucleic acid-containing sample such as is contained in, for example, tissues at the single cell level. Such techniques have been used for karyotyping applications, as well as for detecting the presence, absence and/or arrangement of specific genes contained in a cell. However, for karyotyping, the cells in the sample typically are allowed to proliferate until metaphase (or interphase) to obtain a "metaphase-spread" prior to attaching the cells to a solid support for performance of the in situ hybridization reaction.

Briefly, fluorescence in situ hybridization involves fixing the sample to a solid support and preserving the structural integrity of the components contained therein by contacting the sample with a medium containing at least a precipitating agent and/or a cross-linking agent. Exemplary agents useful for "fixing" the sample are described in the Examples. Alternative fixatives are well known to those of ordinary skill in the art and are described, for example, in the above-noted patents and/or patent publications.

In situ hybridization is performed by denaturing the target nucleic acid so that it is capable of hybridizing to a complementary probe contained in a hybridization solution. The fixed sample may be concurrently or sequentially contacted with the denaturant and the hybridization solution. Thus, in a particularly preferred embodiment, the fixed sample is contacted with a hybridization solution which contains the denaturant and at least one oligonucleotide probe. The probe has a nucleotide sequence at least substantially complementary to the nucleotide sequence of the target nucleic acid. According to standard practice for performing fluorescence in situ hybridization, the hybridization solution optionally contains one or more of a hybrid stabilizing agent, a buffering agent and a selective membrane pore-forming agent. Optimization of the hybridization conditions for achieving hybridization of a particular probe to a particular target nucleic acid is well within the level of the person of ordinary skill in the art.

In reference to a probe, the phrase "substantially complementary" refers to an amount of complementarity that is sufficient to achieve the purposes of the invention, i.e., that is sufficient to permit specific hybridization of the probe to the nucleic acid target while not allowing association of the probe to non-target nucleic acid sequences under the hybridization conditions employed for practicing the invention. Such conditions are known to those of ordinary skill in the art of in situ hybridization.

The genetic abnormalities for which the invention is useful are those for which there is an aberration in the number and/or arrangement of one or more chromosomes with respect chromosomes obtained from an individual having a normal chromosome complement. Exemplary chromosomes that can be detected by the present invention include the human X chromosome, the Y chromosome and chromosomes 13, 18 and 21. For example, the target nucleic acid can be an entire chromosome, e.g., chromosome 21, wherein the presence of three copies of the chromosome ("the distribution" of the target nucleic acid) is indicative of the genetic abnormality, Down syndrome). Exemplary probes that are useful for specifically hybridizing to the target nucleic acid (e.g. chromosome) are probes which can be located to a chromosome(s) that is diagnostic of a genetic abnormality. See e.g., Harrison's Principles of Internal Medicine, 12th edition, ed. Wilson et al., McGraw Hill, N.Y., N.Y. (1991).

The preferred embodiment of the invention is directed to the prenatal diagnosis of Down syndrome by detecting trisomy 21 (discussed below) in fetal cells present in, for example, maternal peripheral blood, placental tissue, chorionic villi, amniotic fluid and embryonic tissue. However, the method of the invention is not limited to analysis of fetal cells. Thus, for example, cells containing the target nucleic acid may be eukaryotic cells (e.g., human cells, including cells derived from blood, skin, lung, and including normal as well as tumor sources); prokaryotic cells (e.g., bacteria) and plant cells. According to one embodiment, the invention is used to distinguish various strains of viruses. According to this embodiment, the target nucleic acid may be in a non-enveloped virus or an enveloped virus (having a non-enveloped membrane such as a lipid protein membrane). See, e.g., Asgari supra. Exemplary viruses that can be detected by the present invention include a human immunodeficiency virus, hepatitis virus and herpes virus.

The oligonucleotide probe is labeled with a fluorophor (fluorescent "tag" or "label") according to standard practice. The fluorophor can be directly attached to the probe (i.e., a covalent bond) or indirectly attached thereto (e.g., biotin can be attached to the probe and the fluorophor can be covalently attached to avidin; the biotin-labeled probe and the fluorophor-labeled avidin can form a complex which can function as the fluorophor-labeled probe in the method of the invention).

Fluorophors that can be used in accordance with the method and apparatus of the invention are well known to those of ordinary skill in the art. These include 4,6-diamidino-2-phenylindole (DIPA), fluorescein isothiocyanate (FITC) and rhodamine. See, e.g., the Example. See also U.S. Pat. No. 4,373,932, issued Feb. 15, 1983 to Gribnau et al., the contents of which are incorporated herein by reference, for a list of exemplary fluorophors that can be used in accordance with the methods of the invention. The existence of fluorophors having different excitation and emission spectrums from one another permits the simultaneous visualization of more than one target nucleic acid in a single fixed sample. As discussed below, exemplary pairs of fluorophors can be used to simultaneously visualize two different nucleic acid targets in the same fixed sample.

The distribution of the target nucleic acid is indicative of the genetic abnormality. See e.g., Asgari supra. The genetic abnormalities of the invention include deletions, additions, amplifications, translocations and rearrangements. For example, a deletion is identified by detecting the absence of the fluorescent signal in the optical field. To detect a deletion of a genetic sequence, a population of probes are prepared that are complementary to a target nucleic acid which is present in a normal cell but absent in an abnormal one. If the probe(s) hybridize to the nucleic acid in the fixed sample, the sequence will be detected and the cell will be designated normal with respect to that sequence. However, if the probes fail to hybridize to the fixed sample, the signal will not be detected and the cell will be designated as abnormal with respect to that sequence. Appropriate controls are included in the in situ hybridization reaction in accordance with standard practice known to those of ordinary skill in the art.

A genetic abnormality associated with an addition of a target nucleic acid can be identified, for example, by detecting binding of a fluorophor-labeled probe to a polynucleotide repeat segment of a chromosome (the target nucleic acid). To detect an addition of a genetic sequence (e.g., trisomy 21), a population of probes are prepared that are complementary to the target nucleic acid. Hybridization of the labeled probe to a fixed cell containing three copies of chromosome 21 will be indicated as discussed in the Examples.

Amplifications, translocations and rearrangements are identified by selecting a probe which can specifically bind to the nucleic acid target for which amplification, translocation or rearrangement is suspected and performing the above-described procedures. In this manner, a fluorescent signal can be attributed to the target nucleic acid which, in turn, can be used to indicate the presence or absence of the genetic abnormality in the sample being tested.

Each of the above-identified patents, patent publications and references is incorporated in its entirety herein by reference.

EXAMPLES

Sample Preparation (1) Slide Preparation

Fresh lymphoblasts were obtained from patients according to standard procedures known to those of ordinary skill in the art. In general, between about 10 and about 20 ml of peripheral maternal blood is used for analysis. Twenty mls of maternal blood (containing about 100 fetal cells) was centrifuged onto glass slides, for 5 minutes at 5000 rpm. The slides were dipped in chilled 80% ethanol/water (v/v) for 5 minutes, air dried and stored. Alternatively, other useful fixatives can be used, including, e.g., acetic acid, methanol, acetone, and combinations thereof, for example ethanol/methanol mixture 3:1 (v/v).

(2) Fluorescence in Situ Hybridization

Slides were stored for up to two weeks at room temperature before hybridization. Cell preparations were heat denatured in 2× SSC (0.3 M NaCl, 30 mM Na citrate)-70% formamide at 70° C. for two minutes, dehydrated through 70%, 90% and 100% alcohol and air dried at room temperature. Hybridization buffer (50% formamide/10% dextran sulphate in 2× SSC pH 7.0) containing the probe was denatured at 70° C. for seven minutes and cooled on ice at 4° C. according to standard hybridization procedures. An aliquot of the hybridization solution was added to each slide under a sealed coverslip and incubated overnight in a moist chamber at 37° C. The coverslips were removed in 2× SSC and the slides washed in 50% formamide/2× SSC (pH 7.0) at 45° C. for forty minutes, twice in 2× SSC (pH 7.0) for five minutes at room temperature and once in 1× SSC (pH 7.0) for five minutes at room temperature. Slides were stored at room temperature in phosphate buffer (0.1 M $NaH_2PO_4$, 0.1 M $Na_2HPO_4$ pH 8.0).

Detection: When fluoroscein is the probe dye, the dye is first excited with light having a wavelength of 488 nm and then the emitted light is measured. For the emitted light, a 540 bp filter is used, i.e., only light with a wavelength between 520 and 560 nm is allowed to pass. The method of detection and the apparatus used therefor are disclosed here. At this point, it is noted that the emitted light is filtered before arriving at a detection apparatus or a human observer. Such filtering is a standard procedure of florescence microscopy. This pre-detection filtering is not specifically part of the image processing methods of the present invention, but is rather a conventional preprocessing step.

PREFERRED EMBODIMENT

Apparatus

An apparatus according to one embodiment of the present invention is now described in connection with FIG. 1. FIG. 1 shows the basic elements of a system according to this embodiment. The basic elements of the system include an X-Y stage 101, a mercury light source 103, a fluorescence microscope 105, a color, chilled-CCD camera 107, a personal computer (PC) 109, and one or more monitors, e.g. 111 and 113. The individual elements of the system may be custom-built or purchased off-the-shelf as standard components. These elements will now be described in somewhat greater detail.

The X-Y stage 101, is a positionable stage suitable for use with microscope 105. For example, X-Y stage 101 may be a manual stage having conventional micrometer adjustments for positioning a microscope slide, by a human operator. Alternatively, X-Y stage 101 may be controlled by the PC 109, using a software program executing in the PC. Such a PC-controlled X-Y stage 101 may therefore include a stage controller circuit card 101, plugged into an expansion bus of the personal computer 109. Electronically controlled stages such as described here are produced by microscope manufacturers, including Olympus (Tokyo, Japan) as well as other manufacturing concerns.

The microscope 105 may be any fluorescence microscope equipped with a reflected light fluorescence illuminator and suitable lenses. For example, the microscope is preferably equipped with an oil immersion 100× objective lens, providing a total magnification between about 600× and 1000×. It is known that fluorescence images obtained by such a microscope have a decreasing light intensity from the center to the boundary of the optical field. The mercury light source 103 is therefore capable of providing consistent and substantially uniform illumination of a sample which produces a fluorescence image viewed through the microscope 105.

The image is viewed by camera 107. The camera 107 is a color, chilled, 3-chip CCD camera providing high sensitivity and resolution. Chilling of the CCD, for example, thermo-electric chilling, minimizes the dark current generated during long time exposure, i.e., it increased the signal-to-noise ratio of the CCD. This enables extremely high quality images to be captured under low illumination and exposure times as long as 5 seconds. A suitable camera is a HAMAMATSU (HAMAMATSU PHOTONICS K.K., HAMAMATSU CITY, JAPAN, model C5820-10). The Hamamatsu camera is a PAL, color, chilled-CCD camera with a resolution of 739×512 pixels capable of exposure times up to 10 seconds. The output of camera 107 is fed to a frame grabber and image processor circuit 117 installed in the PC 109. Of course, other cameras and camera technologies may be suitable if sufficient sensitivity and resolution are available to obtain images which may be processed as discussed below.

The frame grabber and image processor circuit 117 may be, for example, a combination of a MATROX IM-CLD color image capture module and a MATROX IM-640 image processing module, featuring hardware-supported image processing capabilities. Thus, it executes SIMPLE-based software instructions high speeds, because the SIMPLE software program, available from COMPIX, INC. IMAGING SYSTEMS (Mars, Pa.), has been designed to take advantage of the MATROX hardware capabilities. The MATROX boards support a dedicated SVGA monitor 113. Any SVGA monitor suitable for use with the image processing boards can be used. In this embodiment, the dedicated monitor 113 is a ViewSonic 4E SVGA monitor, from ViewSonic (Walnut, Calif.).

In order to have sufficient processing and storage capabilities available, it is preferred that the PC 109 be an INTEL 486-based PC having at least 8 MB RAM and at least 200 MB of hard disk drive storage space (INTEL is a registered trademark of the Intel Corporation). The PC 109 of the present embodiment further includes a monitor 111. Other than the specific features described herein the PC 109 is conventional, and can include keyboard, printer or other desired peripheral devices not shown. Also, PCs of greater or lesser specifications may be used, with a commensurate increase or decrease in capability to be expected.

Method

The PC 109 executes a software program called SIMPLE which controls operation of the frame grabber and image processor circuit 117. SIMPLE also processes images captured by frame grabber and image processor circuit 117 and subsequently stores images and processed data in PC 109 as disk files. SIMPLE provides an icon-based environment with specialized routines particularly suitable for performing such image processing tasks as filtering, object selection and measurement. Most of the SIMPLE tasks are directed by a human operator using a pointing device connected to PC 109, such as a mouse or trackball (not shown).

In order to process images using SIMPLE, a number of image calibration steps must first be taken.

Figure 2:
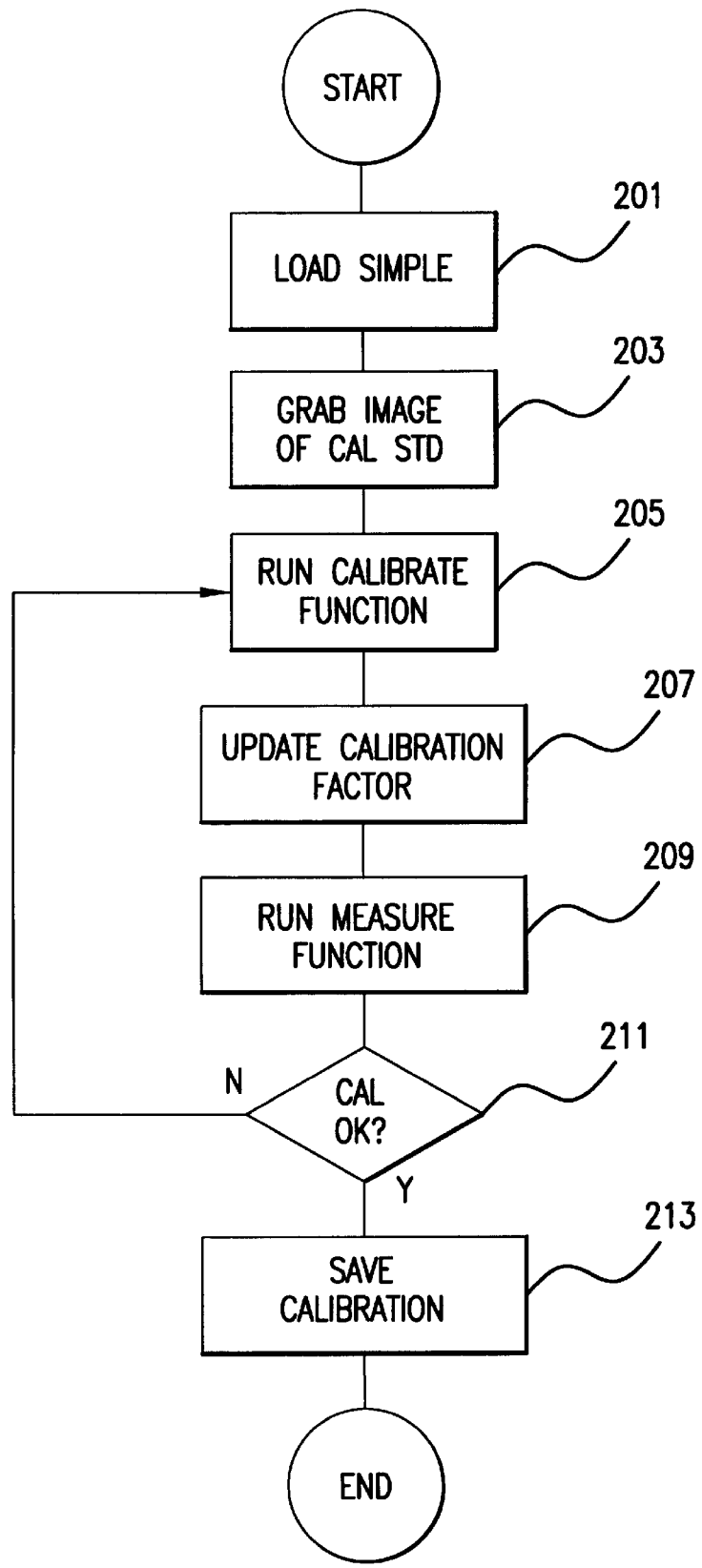
FIG. 2 is a flowchart of the calibration steps of one embodiment of the invention.

The flowchart of FIG. 2 shows the calibration steps of this embodiment of the present invention. Calibration modifies parameters of the software program to compensate for day to day variation in system performance, as well as variations from one microscope 105, camera 107, and other system components to another.

In particular, calibration is directed to determining image magnification so that accurate size measurements may be made. Object size measurements in SIMPLE are initially made in pixels. The operator can calibrate the image using a distance calibration standard such as a microscope graticule or other solid support, e.g., a culture plate or a well having known, fixed distances marked thereon, as follows. In step 201, the SIMPLE Image Capture utility is loaded into the PC 109 for execution. An image of a microscope graticule slide (or other distance calibration standard) is then grabbed, step 203, using the microscope 105 and the camera 107 using a specific, nominal total magnification, e.g., a 10× ocular and a 40× objective lens. This image is processed in the processing board. Selecting the SIMPLE CALIBRATE function, step 205, causes a cursor to appear on the image monitor. The cursor is moved in response to operator input made using the pointing device to the start of the known distance and that point designated by the operator. The cursor is then moved, causing the SIMPLE software program to draw a rubber-band like line which the operator then joins to the other end of the known distance, whereupon that point is also designated. Then the operator answers the question "How long is the line" by entering the number of calibration units indicated by the line. A calibration factor is thus updated, step 207. The MEASURE function may now be selected to check the calibration, step 209. Selecting the function will cause the cursor to again appear on the monitor. The cursor is moved to the first point of a distance to be measured, which is designated, then the rubber-band line is dragged to the other end of the distance to be measured, which is designated. The measured distance is verified, step 211. If the measured distance does not match the actual distance, then control may be returned to step 205 to re-calibrate. Otherwise, the current calibration is saved by selecting a DISK SAVE function, step 213. Multiple calibration files can be saved to be used in future applications, for example employing different lens combinations.

The automated analysis employs two principal procedures: a preprocessing procedure and a main procedure. Except where noted, the steps of the procedures are performed by the computer executing SIMPLE software instructions to carry out the functions named. The functions named are available directly in simple, as named commands.

A new slide properly stained using the fluorescence in situ hybridization (FISH) technique is placed under the fluorescence microscope. The objects of interest which are to be recognized, i.e., the nuclear or chromosomal areas, have specific chromatic features. Multiple targets can be delineated simultaneously in a particular specimen by combining fluorescence detection procedures. That is, if different targets are labeled with different fluorophors that fluoresce at different wavelengths, then the software program can be made to separately identify objects emitting the different fluorophors, provided full color information is available in the image. Targets with differing affinities for different fluorophors may be differentiated by the color combinations emitted. Each target may emit at wavelengths corresponding to two or more fluorophors, but the intensity of each may differ, for example. Thus, all three color components of the microscopic images are used during processing.

Figure 3:
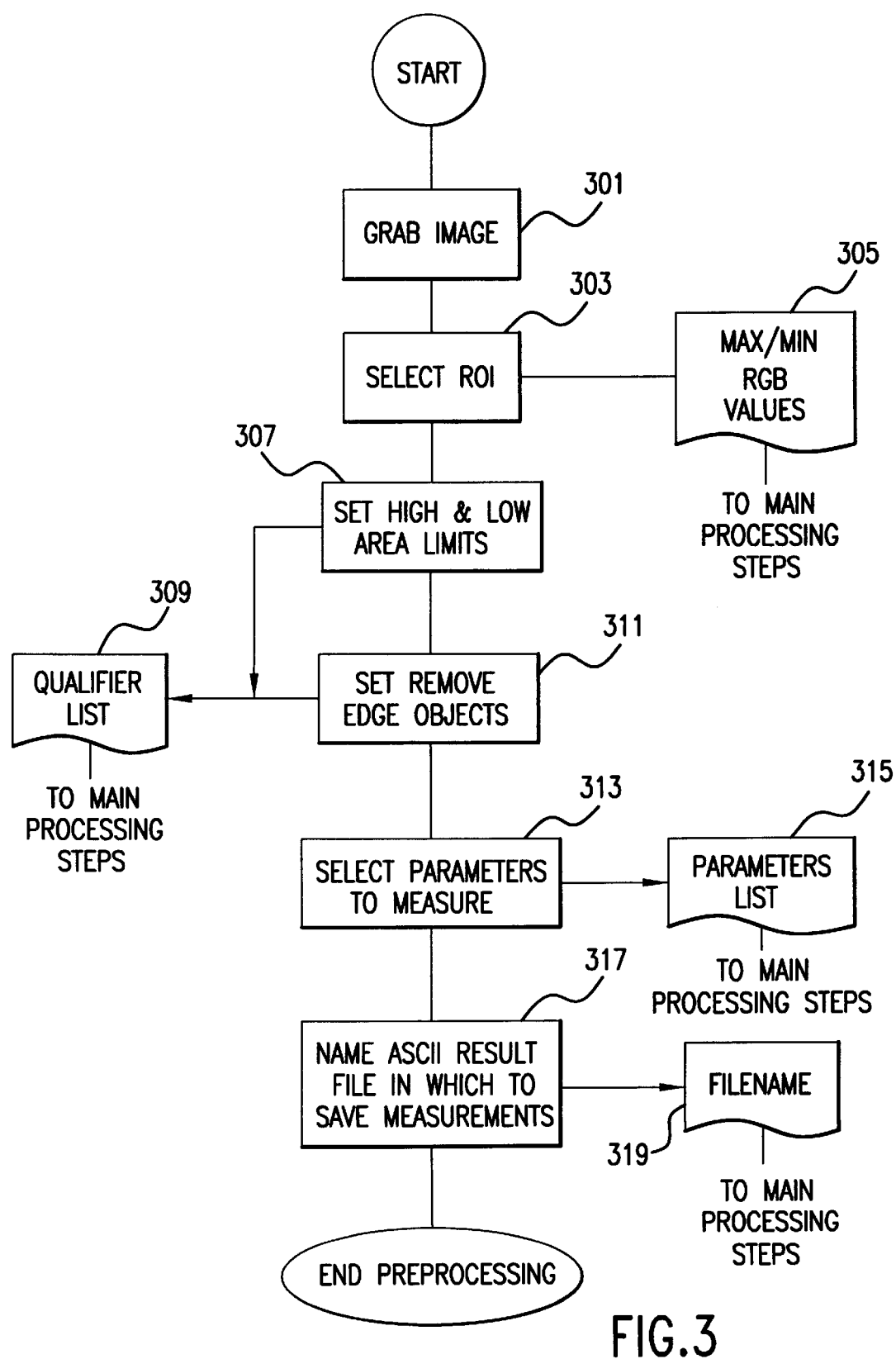
FIG. 3 is a flowchart of the preprocessing steps of one embodiment of the invention.

For each new specimen inserted under the microscope, a preprocessing procedure is first executed. The flowchart of FIG. 3 shows the preprocessing steps of this embodiment of the present invention. Preprocessing permits the software to compensate for specimen-to-specimen variations.

Preprocessing

Preprocessing produces a number of results which are required by subsequent steps performed as part of the main processing steps. These results are passed from the preprocessing steps to the main processing steps by any conventional means, such as storing them in RAM or on disk.

A microscope image is first grabbed by the frame grabber and image processing circuits (FIG. 1, 117), step 301. The specimen has been prepared and placed in the optical path of the microscope in such a way that the image grabbed includes one or more interphase nuclei or a mixture of interphase nuclei and metaphase chromosomes. Next, a region of interest (ROI) is manually selected using the pointing device, step 303, to include intracellular, cytoplasmic and nuclear image portions, but to exclude fluorescent areas of the nucleus, i.e. interesting objects. For the regions not of interest which have been selected, maximum and minimum values of the red, green and blue components of the pixels of those regions are determined. The maximum and minimum red, green and blue values 305 are then passed to the main processing steps. In step 307, high and low area limits are set which define the largest and smallest chromosomal areas to be recognized. The high and low area limits are placed on a qualifier list 309, which is also passed to the main processing steps. Also placed on the qualifier list 309 is an indication or flag that the remove edge objects function has been set, step 311. In subsequent processing, the remove edge objects function will cause objects whose boundaries intersect the edge of the image to be removed from the regions to be considered. The parameters of selected objects which are to be measured are then selected, step 313, and placed on parameter list 315. Parameter list 315 is also passed to the main processing steps. Finally, the operator selects a name for an ASCII result file in which parameter measurements are saved, step 317. The file name, 319, is passed to the main processing steps.

Parameters which may be selected to be measured and placed on parameter list 315 may include such values of interest as the area of the object and the mean red, green and blue intensity values within the object. By choice of parameters to be placed on parameter list 315 and the values of qualifiers placed on qualifier list 309. The present invention may be applied to the taking of other measurements or the making of other determinations than those to which the specific embodiment described has been applied. For example, by changing the high and low area limits placed on qualifier list 309, objects of different sizes than the size of a chromosome may be detected. Likewise, the parameters noted in connection with the present embodiment are suitable for distinguishing between particular fluorescent labels applied to particular chromosomes and which fluoresce at different wavelengths. However, other parameters could be measured which are suitable for making other determinations concerning the detected image.

After preprocessing, the system performs the automated analysis by the repeated execution of the main procedure.

Figure 4:
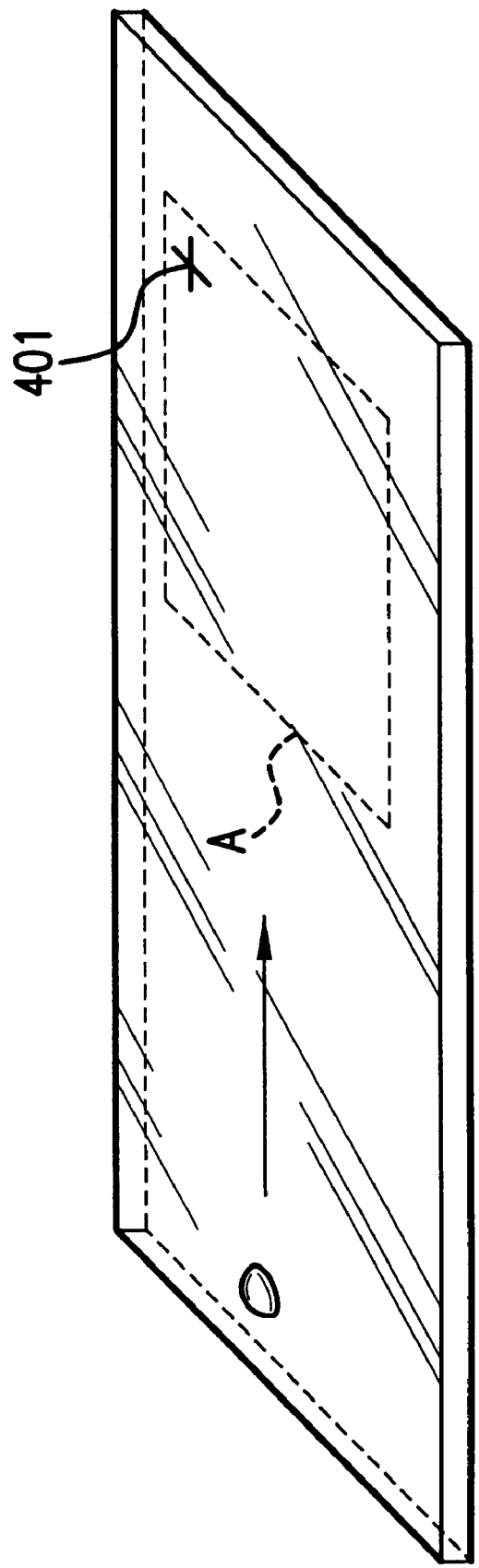
FIG. 4 is an illustration of a microscope slide showing an area of observation.
Figure 5A:
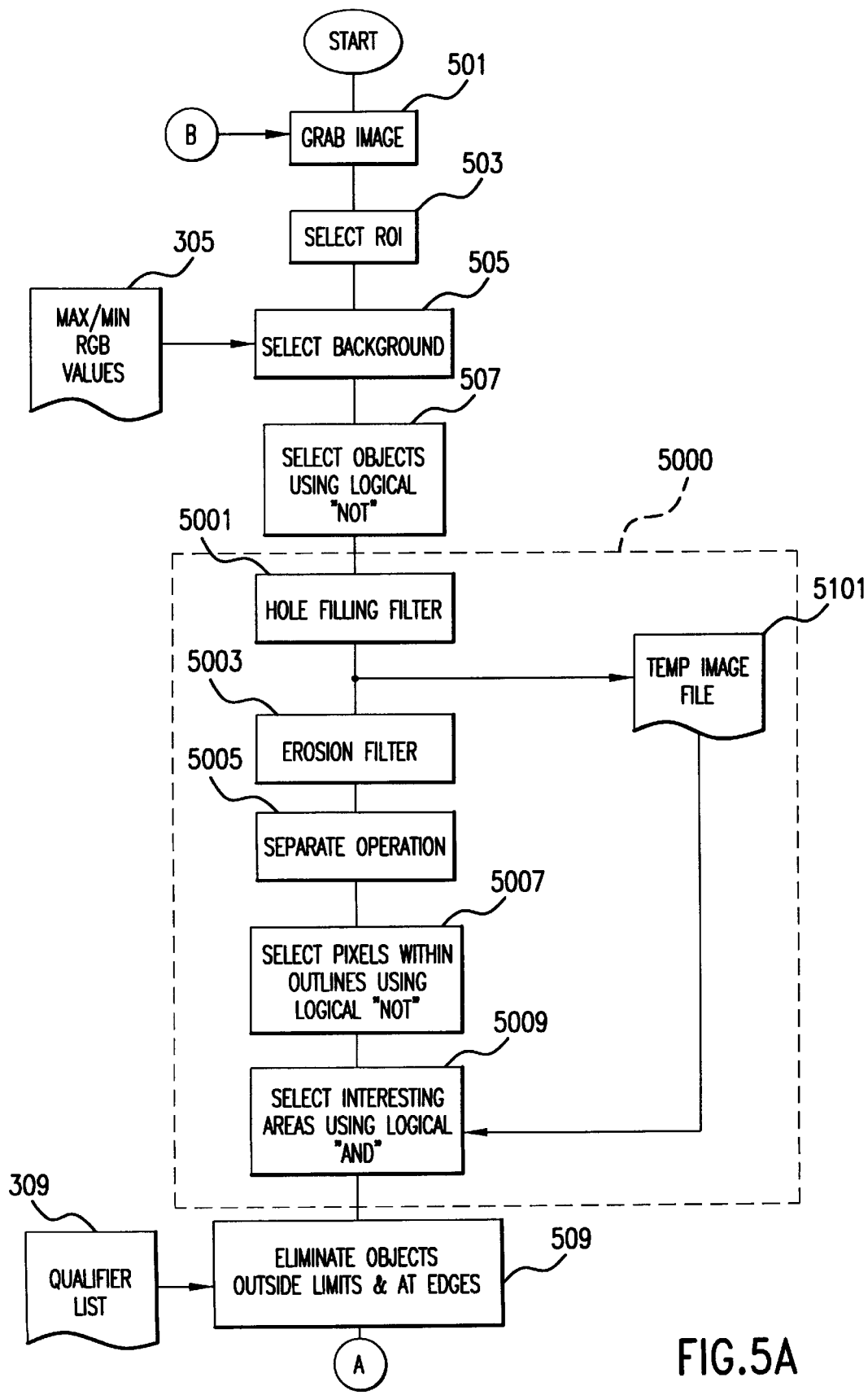
FIGS. 5A and 5B are a flowchart of the main processing steps of one embodiment of the invention.
Figure 5B:
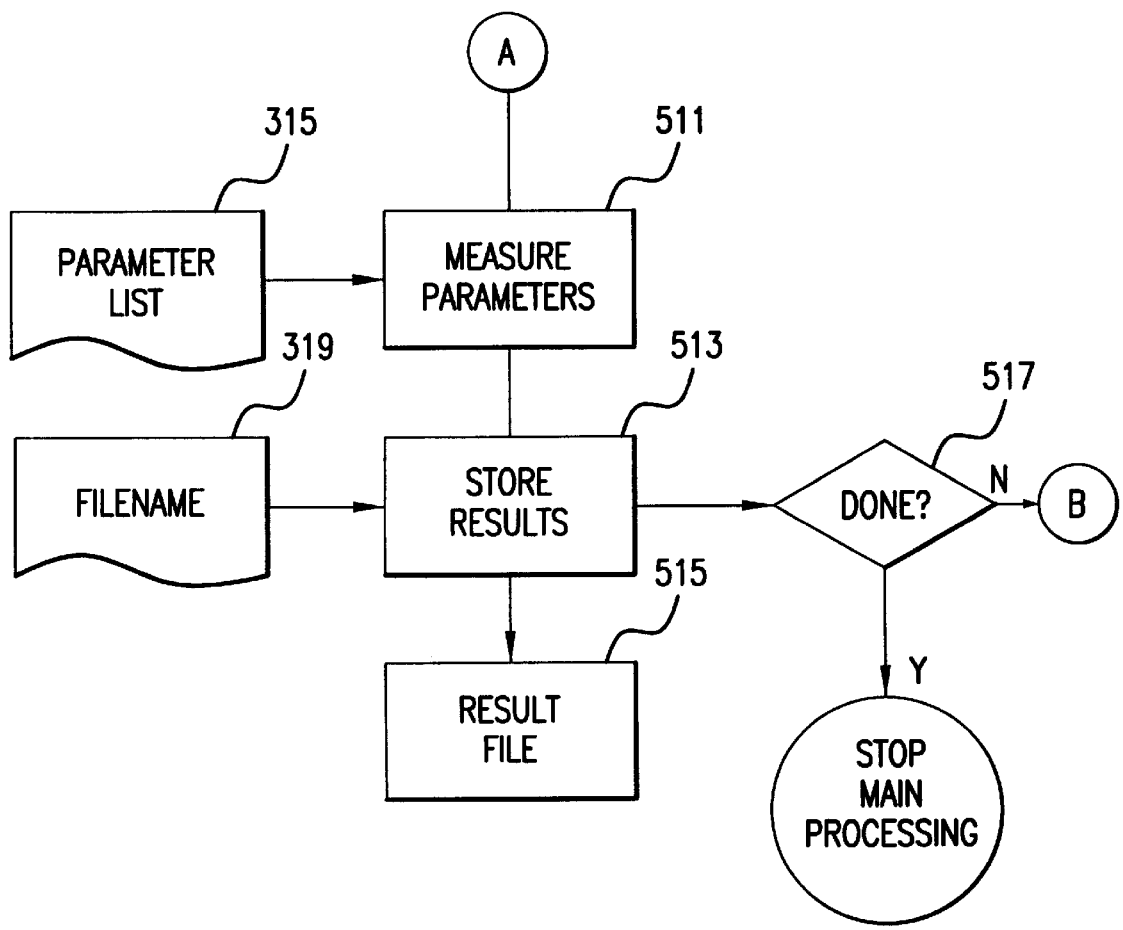

The slide containing the FISH-treated cells is positioned into the X-Y stage 101. The X-Y stage 101 is moved to an initial observation position (FIG. 4, 401). A processing loop is executed repeatedly until either a predetermined number of cells of a particular type have been identified and measured or an entire area of best observation (FIG. 4, A) has been analyzed. In the application for which the present embodiment is intended, identifying multiple targets of chromosomal DNA, the loop would preferably be executed until 100 nuclei have been processed. Each nucleus is manually selected in the successive optical fields. Data representing the measurement of the chromosomal areas within those nuclei are collected in an ASCII file.

Execution of the processing loop is controlled by the operator who selects the nuclear areas to be processed through manual delineation of a wider area containing the nucleus, i.e., a wide Region Of Interest (ROI) containing only the nuclear area in which the chromosomal areas are to be counted.

The computer instructions defining the main processing procedure are contained in a "work" file which is executed automatically. The instructions include instructions to suspend execution for the operator to select the Region of Interest containing the nucleus. The main processing procedure is now described in detail.

Main Procedure

Using the apparatus described above in connection with the SIMPLE software system, the main processing steps first grab an image of the prepared slide, step 501, which includes at least one nucleus containing fluorescing regions. An ROI containing a single nucleus having fluorescence regions is then selected, step 503. The selection is conventionally performed using the pointing device. In step 505, the image is automatically processed to select the background, or non-interesting portions of the ROI, by using the maximum and minimum red, green and blue values 305 passed from the preprocessing procedure, step 505. That is, those pixels whose red, green and blue intensity values fall between the maximum and minimum values obtained in preprocessing are selected as part of the background. At this point, the background is selected and the objects of interest are not selected. Therefore, a logical NOT operator is applied to the selection, causing the objects to be selected rather than the background, step 507. A set of complex filtering steps, steps 5000, described below, are applied to generate a final selection of those areas considered interesting, in that they contain the fluorescent objects desired to be measured. The qualifier list 309 is then applied against the characteristics of the objects remaining, to eliminate objects outside the high and low area limits and also to eliminate those objects on the edges of the region of interest, step 509. The parameters contained on parameter list 315 are then measured at step 511, and the results stored, step 513, in a result file 515 having the file name 319 determined by the preprocessing steps. At this point, either the operator or a counter in the software program determines whether the main processing steps have been performed a sufficient number of times, and main processing is done, step 517. If it is determined that additional passes through the main processing steps are required, then control passes to step 501, wherein a new image is grabbed.

The above-described main processing steps are repeated until a statistically significant number of samples have been measured. For example, in order to detect the genetic abnormality of a trisome of chromosome 21, 100 cell nuclei should be measured, requiring 100 passes through the main processing steps.

The filtering steps 5000 operate on a pixel-by-pixel basis, as follows. In step 5001, a hole filling filter is applied to the image. This filter, available through the SIMPLE language, determines when dark holes have appeared within the lighter fluorescent chromosomes by searching for dark areas within light objects. Those areas are lightened up. The output of the hole filling filter is held in a temporary image file 5101, as well as being used as the input to the erosion filter, step 5003. Erosion filtering, also available through the SIMPLE language, replaces the center pixel of a small kernel with the darkest pixel in the kernel. In the preferred embodiment, the kernel used is 3×3. A separate operation, step 5005 is next performed, to grow the objects until they meet, but do not merge. This step also creates outlines, defining the edges of all the objects. A logical NOT operation, step 5007, causes the pixels within the outlines to become selected rather than the outlines. Finally, in step 5009, the result of step 5007 is logically ANDed with the stored temporary image file 5101. This causes only those pixels which are defined in both the temporary image file 5101 and the output of step 5007 to be retained.

If a combination of fluorescence detection procedures is used, more than two chromosomal areas may be detected per nucleus. Therefore, it is possible to recognize two chromosomal areas relative to chromosomes 21, another two relative to chromosome 18, one relative to chromosome X and one relative to chromosome Y, enabling the discovery of possible numerical aberrations detected by the enumeration of hybridization signals. The enumeration of the hybridization signals is executed after completing the measurement of 100 nuclei through an application program external to SIMPLE, compiled using CLIPPER (COMPUTER ASSOCIATES, CA). This program reads the measurement results ASCII file and classifies the chromosomal areas detected according to their RGB color combination. When two or more different fluorophors are used in combination, different combinations of RGB color values may be used to distinguish different targets, some targets of which may be labeled by more than one fluorophor. For example, targets may be stained with red and green fluorophors, but one target may receive fluorophors to emit 30% red and 70% green, another target may receive fluorophors to emit 70% red and 30% green, while a third target may receive fluorophors to emit only red. The three targets may be distinguished on the basis of their relative emissions. If the number of signals indicative of a chromosomal area corresponding to a specific chromosome, e.g., chromosome 21, is greater than two to an operator-selected statistically significant level, then a report is issued identifying an increased likelihood for trisomy 21 in the specific sample.

Although the present invention has been described in connection with the clinical detection of chromosomal abnormalities in a cell-containing sample, the image processing methods disclosed herein has other clinical applications. For example, the image processing steps described can be used to automate a urinalysis process. When the techniques of the present application are combined with those of application Ser. No. 08/132,804, filed Oct. 7, 1993, a wide variety of cell types can be visualized and analyzed, based on their morphology. Cell morphology can be observed for the purpose of diagnosing conditions for which cell morphology has been correlated to a physiological condition. Such conditions are known to those of skill in the art. See, e.g., Harrison, supra. Various cell characteristics and abnormalities may be detected based on these techniques. Finally, it should be noted that the particular source of the sample is not a limitation of the present invention, as the sample may be derived from a blood sample, a serum sample, a urine sample or a cell sample from the uterine cervix. The cell visualization and image analysis techniques described herein may be used for any condition detectable by analysis of individual cells, either by morphology or other characteristics of the isolated cells.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto.

What is claimed is:

1. A computer software product comprising a computer readable storage medium having fixed therein a sequence of computer instructions directing a computer system to detect whether a genetic abnormality is present in a fixed sample containing at least one target nucleic acid, the instructions directing steps of:
   receiving a digitized color image of the fixed sample, which has been subjected to fluorescence in situ hybridization under conditions to specifically hybridize a fluorophor-labeled probe to the target nucleic acid;
   processing the color image in a computer to separate objects of interest from background;
   measuring size and color parameters of the revised objects of interest so as to identify and enumerate objects having specific predetermined characteristics associated with the target nucleic acid; and
   analyzing the enumeration of objects with respect to a statistically expected enumeration to detect whether the genetic abnormality is present
   wherein the step of processing comprises the steps of:
      passing the color image through a hole filling filter;
      passing the filled color image through an erosion filter;
      operating on the eroded filled color image to define outlines around areas;
      selecting pixels within the outlines by performing a logical NOT operation; and performing a logical AND operation between the selected pixels and the filled color image.

2. A method of operating a computer system to detect whether a genetic abnormality is present in a fixed sample containing at least one target nucleic acid, the method comprising:
   receiving a digitized color image of the fixed sample, which has been subjected to fluorescence in situ hybridization under conditions to specifically hybridize a fluorophor-labeled probe to the target nucleic acid;
   processing the color image in a computer to separate objects of interest from background;
   measuring size and color parameters of the objects of interest so as to identity and enumerate objects having specific predetermined characteristics associated with the target nucleic acid; and
   analyzing the enumeration of objects with respect to a statistically expected enumeration to detect whether the genetic abnormality is present;
   wherein the step of processing comprises the steps of:
      passing the color image through a hole filling filter;
      passing the filled color image through an erosion filter;
      operating on the eroded filled color image to define outlines around areas;
      selecting pixels within the outlines by performing a logical NOT operation; and performing a logical AND operation between the selected pixels and the filled color image.

3. The product of claim 1, wherein the genetic abnormality is human trisomy 21.

4. The product of claim 1, wherein the step of processing further includes steps of:
   manually selecting a plurality of pixels within the background;
   determining color intensity value ranges corresponding to the portion of the background; and
   identifying as the background those areas of the image having color intensity values within the ranges determined.

5. A method of operating a computer to count occurrences of a target substance in a cell containing sample which has been labeled with a target-specific fluorophor, the method comprising:
   receiving a digitized color image of the fluorophor-labeled sample;
   obtaining a color image of the fluorophor-labeled sample;
   separating objects of interest from background in the color image;
   measuring parameters of the objects of interest so as to enumerate objects having specific characteristics; and
   analyzing the enumeration of objects with respect to a statistically expected enumeration to determine whether said expected enumeration associated with the target substance is present;
   wherein the step of separating comprises the steps of:
      passing the color image through a hole filling filter;
      passing the filled color image through an erosion filter;
      operating on the eroded filled color image, to define outlines around areas;
      selecting pixels within the outlines by performing a logical NOT operation; and performing a logical AND operation between the selected pixels and the filled color image.

6. The method of claim 5, wherein the target substance is human chromosome 21.

7. The method of claim 5, wherein the step of separating further includes steps of:
   manually selecting a plurality of pixels within the background;
   determining color intensity value ranges corresponding to the portion of the background; and
   identifying as the background those areas of the image having color intensity values within the ranges determined.

8. A computer software product comprising:
   a computer readable storage medium having fixed therein a sequence of computer instructions directing a computer system to count occurrences of a target substance in a cell-containing sample which has been labeled with a target-specific fluorophor, the instructions directing steps of:
   receiving a digitized color image of the fluorophor-labeled sample;
   obtaining a color image of the fluorophor-labeled sample;

separating objects of interest from background in the color image;
wherein the step of separating comprises the steps of:
passing the color image through a hole filling filter;
passing the filled color image through an erosion filter;
operating on the eroded filled color image, to define outlines around areas;
selecting pixels within the outlines by performing a logical NOT operation; and performing a logical AND operation between the selected pixels and the filled color image
measuring parameters of the objects of interest so as to enumerates object having specific characteristics; and
analyzing the enumeration of objects with respect to a statistically expected enumeration to determine whether said expected enumeration of target substance is present.

9. The product of claim 8, wherein the step of separating further includes steps of:
manually selecting a plurality of pixels within the background;
determining color intensity value ranges corresponding to the portion of the background; and
identifying as the background those areas of the image having color intensity values within the ranges determined.

10. Apparatus for analyzing an image of a cell-containing sample which has been labeled with a target-specific fluorophor associated with a genetic abnormality, comprising a computer system on which image processing software executes; and
a storage medium in which is fixed a sequence of image processing instructions including
receiving a digitized color image of the fluorophor-labeled sample,
obtaining a color image of the fluorophor-labeled sample,
separating objects of interest from background in the color image,
wherein the step of separating comprises the steps of:
passing the color image through a hole filling filter;
passing the filled color image through an erosion filter;
operating on the eroded filled color image, to define outlines around areas;
selecting pixels within the outlines by performing a logical NOT operation; and performing a logical AND operation between the selected pixels and the filled color image;
measuring parameters of the objects of interest so as to enumerate objects having specific characteristics, and
analyzing the enumeration of objects with respect to a statistically expected enumeration to determine presence of the genetic abnormality.

11. The method of claim 2, wherein the genetic abnormality is in human chromosome X, Y, 13, 18 or 21.

12. The product of claim 1, wherein the genetic abnormality is in human chromosome X, Y, 13, 18 or 21.

13. The method of claim 5, wherein the target substance is human chromosome X, Y, 13, 18 or 21.

14. The product of claim 8, wherein the target substance is human chromosome X, Y, 13, 18 or 21.

15. The apparatus of claim 10, wherein the genetic abnormality is in human chromosome X, Y, 13, 18 or 21.

16. The method of claim 2, wherein the genetic abnormality is human trisomy 21.

17. The product of claim 1, wherein the genetic abnormality is human trisomy 21.

18. The method of claim 5, wherein the target substance is human chromosome 21.

19. The product of claim 8, wherein the target substance is human chromosome 21.

20. The apparatus of claim 10, wherein the genetic abnormality is human trisomy 21.

* * * * *